(12) United States Patent
Avraham et al.

(10) Patent No.: US 12,138,494 B2
(45) Date of Patent: *Nov. 12, 2024

(54) PORTABLE SYSTEM FOR THE PRODUCTION OF OXYGEN

(71) Applicant: Oxygenium Ltd., Ness Ziona (IL)

(72) Inventors: Liraz Avraham, Beit-Shean (IL); Ran Miron, Kadima (IL); Oded Weiss, Great Neck, NY (US); Ben (Binyamin) Alkahe, Mikhmoret (IL)

(73) Assignee: Oxygenium Ltd., Ness Ziona (IL)

( * ) Notice: Subject to any disclaimer, the term of this patent is extended or adjusted under 35 U.S.C. 154(b) by 302 days.

This patent is subject to a terminal disclaimer.

(21) Appl. No.: 17/861,420

(22) Filed: Jul. 11, 2022

(65) Prior Publication Data

US 2022/0347499 A1 Nov. 3, 2022

Related U.S. Application Data

(63) Continuation of application No. 17/379,711, filed on Jul. 19, 2021, now Pat. No. 11,383,109, which is a
(Continued)

(51) Int. Cl.
*A62B 21/00* (2006.01)
*A61M 16/00* (2006.01)
(Continued)

(52) U.S. Cl.
CPC ......... *A62B 21/00* (2013.01); *A61M 16/0051* (2013.01); *A61M 16/024* (2017.08);
(Continued)

(58) Field of Classification Search
CPC ............ C01B 13/0214; C01B 13/0288; A61M 16/00; A61M 16/0051; A61M 16/024;
(Continued)

(56) References Cited

U.S. PATENT DOCUMENTS 2,232,394 A 2/1941 Ko
2,425,669 A 8/1947 Barrington
(Continued)

FOREIGN PATENT DOCUMENTS

CN 107754484 A 3/2018
DE 752731 C 3/1953
(Continued)

OTHER PUBLICATIONS

OSHA Standards for Air Contaminants—29 CFR § 1910.1000, 36 pgs.

*Primary Examiner* — Joseph D. Boecker
(74) *Attorney, Agent, or Firm* — Goodwin Procter LLP

(57) ABSTRACT

A portable oxygen generating system is provided that comprises a reaction chamber, a feed system for providing and controlling hydrogen peroxide solution to the reaction chamber, and a cooling/condensing system for cooling the hot oxygen and water vapor leaving the reactor and condensing and removing water. The portable chemical oxygen generation system produces humidified, breathable oxygen, that is substantially free of hydrogen peroxide and other contaminants, at a controlled flow and temperature over an extended period of time.

19 Claims, 13 Drawing Sheets

Related U.S. Application Data continuation of application No. PCT/IB2020/053228, filed on Apr. 3, 2020.

(60) Provisional application No. 62/828,475, filed on Apr. 3, 2019.

(51) Int. Cl.
*A61M 16/10* (2006.01)
*A62B 7/08* (2006.01)
*A62B 9/00* (2006.01)
*A62D 9/00* (2006.01)
*C01B 13/02* (2006.01)

(52) U.S. Cl.
CPC ........ *A61M 16/10* (2013.01); *A61M 16/1005* (2014.02); *A61M 16/101* (2014.02); *A61M 16/105* (2013.01); *A61M 16/1075* (2013.01); *A62B 7/08* (2013.01); *A62B 9/003* (2013.01); *A62D 9/00* (2013.01); *C01B 13/0214* (2013.01); *C01B 13/0288* (2013.01); *A61M 2016/1025* (2013.01); *A61M 2202/0208* (2013.01); *A61M 2205/3303* (2013.01); *A61M 2205/3334* (2013.01); *A61M 2205/3355* (2013.01); *A61M 2205/3368* (2013.01); *A61M 2205/3592* (2013.01); *A61M 2205/362* (2013.01); *A61M 2205/75* (2013.01); *A61M 2205/8206* (2013.01); *A61M 2230/205* (2013.01); *B01D 2256/12* (2013.01); *B01D 2259/4533* (2013.01); *C01B 2210/0003* (2013.01); *C01B 2210/0012* (2013.01)

(58) Field of Classification Search
CPC .............. A61M 16/10; A61M 16/1005; A61M 16/101; A61M 16/105; A61M 16/107; A61M 16/1075; A61M 16/201; A61M 16/202; A61M 2016/102; A61M 2016/1025; A62B 21/00; A62B 7/08; A62B 9/003; A62D 9/00; B01D 53/268; B01D 2256/12; B01D 2259/4533

See application file for complete search history.

(56) References Cited

U.S. PATENT DOCUMENTS

| | | | |
|---|---|---|---|
| 3,882,223 A | 5/1975 | Reinhardt | |
| 3,917,461 A | 11/1975 | Kuhl et al. | |
| 4,792,435 A * | 12/1988 | Nakajima | A62B 21/00 422/202 |
| 4,861,560 A | 8/1989 | Nakajima | |
| 5,665,316 A * | 9/1997 | Salonia | C01B 13/0214 423/579 |
| 8,147,760 B1 | 4/2012 | Tuvard et al. | |
| 9,242,189 B2 | 1/2016 | Buese et al. | |
| 2005/0022810 A1 | 2/2005 | Moore et al. | |
| 2008/0128259 A1 | 6/2008 | Kostek et al. | |
| 2008/0247926 A1 | 10/2008 | Osterloh | |
| 2015/0144364 A1 | 5/2015 | Barron | |
| 2020/0316415 A1 | 10/2020 | Alkahe et al. | |

FOREIGN PATENT DOCUMENTS

| | | | | |
|---|---|---|---|---|
| EP | 2515061 A1 | 10/2012 | | |
| GB | 2167054 A * | 5/1986 | | B01J 7/02 |
| JP | S62297201 A | 12/1987 | | |
| JP | 2016036773 A | 3/2016 | | |
| KR | 101027904 B1 | 4/2011 | | |
| WO | 96/06799 A1 | 3/1996 | | |
| WO | 97/23413 A1 | 7/1997 | | |
| WO | WO-2009006586 A2 * | 1/2009 | | A61M 16/0045 |
| WO | WO-2018182211 A1 * | 10/2018 | | A61L 9/00 |

\* cited by examiner

PORTABLE SYSTEM FOR THE PRODUCTION OF OXYGEN

CROSS-REFERENCE TO RELATED APPLICATION

This application is a continuation of U.S. patent application Ser. No. 17/379,711, filed Jul. 19, 2021, issuing Jul. 12, 2022, as U.S. Pat. No. 11,383,109, which is a continuation of International Patent Application No.: PCT/IB2020/053228 filed Apr. 3, 2020, which claims the benefit of priority to U.S. Provisional Patent Application No. 62/828,475, filed on Apr. 3, 2019, the contents of each is incorporated herein by reference.

FIELD OF THE INVENTION

This disclosure is in the field of oxygen production, methods of producing oxygen, and chemical oxygen generators. More specifically, this disclosure provides a portable chemical oxygen generator providing high-purity breathable oxygen. The disclosure also provides an apparatus/system for the low-energy condensing of (water) vapor, for example in removing the water by-product of oxygen generation.

BACKGROUND

Oxygen is a critical component of medical treatment. This treatment can be chronic or acute. Supplemental oxygen can be lifesaving in emergency situations, although the burden of providing oxygen during transport and in remote areas is substantial in cost, transport, and materials.

Oxygen cylinders are heavy and present a number of potential hazards including combustion, detonation and projectile risks. Liquid oxygen systems provide a large amount of gas with a smaller footprint, but are heavy, exhaust gas over time, and present a burn risk if handled improperly. In addition, the output of both of these oxygen systems is finite and requires refilling, which presents logistical issues in far forward military operations. Simpler, lighter, and longer lasting oxygen delivery systems are needed for many emergency situations, including military and mass casualty operations.

Portable oxygen concentrators (POCs) and chemical oxygen generators (COGs) have been proposed as a solution. POCs, sometimes referred to as oxygen concentrators draw in air from the environment, which usually contains about 21% oxygen, and extract the nitrogen to supply oxygen at a concentration of up to 90-95%. Portable units generally produce up to 6 l/min and larger devices (not portable) producing up to 25 l/min. All these devices are electrically operated and require a source of continuous power, so a power failure will result in a failure of oxygen supply unless a standby generator, or a battery backup and power inverter are available. Also, the low flow and lower pressure of gas supplied from the portable units limits their use for many emergency situations.

Chemical oxygen generation was first suggested by the work of Joseph Priestly when he discovered oxygen during his work with mercuric oxide. Priestly published his findings in 1775. In 1902, the "Lancet" reported on Kamm's oxygen generator invention for medical use. The device used chlorate as the oxygen source and when heated by a spirit lamp produced approximately 4 cubic ft of oxygen before needing to be replenished with ingredients. Chlorate candles have been used as a source of emergency oxygen, for example in submarines. However, the oxygen-producing reaction of chlorate candles is very hot (about 700-800° C.), and accordingly can be very hazardous.

POCs and COGs have been proposed for use in far forward military operations and in disaster and mass casualty scenarios as alternatives to liquid and pressurized gaseous oxygen systems because of the logistical challenges, weight, and explosive risks associated with liquid and pressurized gaseous oxygen systems. Evaluation of the currently available technologies shows that COGs can operate for only 30 minutes or less, depending on the manufacturer and design, and the inability to adjust output makes the devices unsuitable for continuous clinical care or long-term operation. COGs may also have an oxygen flow rate that is too low for many emergency uses.

More recently, there has been interest in employing this technology in areas where providing oxygen in cylinders or in liquid form is logistically difficult or economically prohibitive such as during combat casualty care, disaster situations, and in extreme rural environments in undeveloped countries. Simpler, lighter, and longer lasting oxygen delivery systems are needed for military and mass casualty operations.

The FDA dictates that a COG must provide a minimum of 6 L/min of oxygen flow for a minimum of 15 min (21 CFR part 868.5440). However, the US Army demands a higher output, where the system must provide 8 L/min for at least 20 min. This is an increase of 75% in the total $O_2$ output, a level not attainable by the available COGs. There exists a long felt need for a portable, on-demand oxygen generator.

SUMMARY OF THE INVENTION

The present disclosure provides a chemical oxygen generation system which produces humidified, breathable oxygen, that is substantially free of hydrogen peroxide and other contaminants, at a controlled flow and temperature over an extended period of time. In an aspect, the chemical oxygen generation system can generate a constant flow of oxygen of more than about 8 L/min and up to about 15 L/min, at a temperature of less than about 40° C. for more than about 30 minutes.

In one aspect, the portable oxygen generating system comprises a reaction chamber, a feed system for providing and controlling hydrogen peroxide solution to the reaction chamber, and a cooling/condensing system for cooling the hot oxygen and water vapor leaving the reactor and condensing and removing water. The reaction chamber comprises a catalyst that facilitates the chemical decomposition of hydrogen peroxide to oxygen and water, an inlet for the introduction of hydrogen peroxide solution into the reaction chamber, and an outlet for the release of oxygen and water vapor from the reaction chamber. The hydrogen peroxide feed system comprises a hydrogen peroxide reservoir that contains aqueous hydrogen peroxide solution and a feed flow regulator for controlling the rate of addition of the aqueous hydrogen peroxide solution into the reaction chamber. The cooling system comprises an inlet for receiving oxygen and water vapor, a condenser comprising two or more drains, each configured to drain water condensed from the water vapor in the cooling system, and an outlet for the release of cooled oxygen gas with reduced water vapor.

It is an aspect of this disclosure to provide a portable device for oxygen generation comprising:
  a. at least one reservoir for holding a hydrogen peroxide solution;

b. one or more reaction chambers containing a catalyst, for reacting hydrogen solution and producing oxygen and water vapor;

c. a feeding system for supplying hydrogen peroxide to the reactor(s) from the reservoir;

d. a system for cooling in fluid communication with the outlet of the reactor, that condenses and removes condensed liquid water;

e. optionally, a drier situated between the reactor and the cooling system for removing a portion of the water from the oxygen stream;

f. optionally, drive system for moving liquid water to a storage tank;

g. optionally, a hydrophobic membrane, for removing water at the oxygen outlet of the cooling system; and h. optionally, an oxygen flow regulator, for regulating oxygen flow at the hydrophobic membrane outlet.

The cooling system may be an open system operatively located between the reactor outlet and the hydrophobic membrane (filter). The cooling system is configured to cool oxygen gas flowing between the reactor and the filter.

It is another aspect to provide a device as presented in any of the above, wherein the reservoir is configured to hold hydrogen peroxide, a hydrogen peroxide complex or a hydrogen peroxide solution.

It is another aspect to provide a device as presented in any of the above, wherein the hydrogen peroxide solution is at least 15% hydrogen peroxide, or is at least 20% hydrogen peroxide. The reservoir may be a cartridge that detachably connects to the feeding system. The cartridge may be configured to be instantly replaceable once the hydrogen peroxide solution is depleted.

It is another aspect to provide a device as presented above, wherein the cartridge attachment system allows rapid attachment to the feeding system. The cartridge may be collapsible, have a collapsible liner, or may be hard-sided or soft-sided.

It is another aspect to provide a device as presented above, wherein the feeding unit is configured to generate pressure on a soft-sided cartridge. The pressure may be generated by a spring, a piston or pneumatic pressure. Additionally or alternatively, the feeding system may comprise a pump, for example a pump selected from a displacement pump, peristaltic pump, syringe pump, piston pump, plunger pump, screw pump and reciprocating pump.

It is another aspect to provide a device as presented in any of the above, wherein the reactor is configured to decompose hydrogen peroxide to water and oxygen. The reactor contains a catalyst that facilitates the chemical decomposition of hydrogen peroxide to oxygen and water. The catalyst may comprise one or more active compounds selected from a metal, a metalloid, an alloy of a metal, an alloy of a metalloid, a compound of a metal and a compound of a metalloid. The catalyst may additionally comprises an electronegative element.

It is another aspect to provide a device as presented in any of the above, wherein the device additionally, and optionally, comprises a catalytic filter. The catalytic filter, if present, may comprise at least one catalyst, the catalyst comprises one or more active compounds selected from a group consisting of a metal, a metalloid, an alloy of a metal, an alloy of a metalloid, a compound of a metal and a compound of a metalloid. The catalytic filter may comprise the same catalyst(s) as the reactor, or may comprise a different catalyst.

It is another aspect to provide a device as presented in any of the above, wherein the cooling system comprises a heat sink. The cooling system may additionally comprise at least one fan for facilitating the removal of heat from the cooling system. The fan may be an electric fan.

It is another aspect to provide a device as presented in any of the above, wherein the cooling system comprises a condenser. The cooling system comprising a condenser is configured to facilitate the draining of liquid water condensed by the cooling system. The draining system may be configured to drain the condensed water from at least one point along cooling system.

It is another aspect to provide a device as presented in any of the above, wherein the condensed water is drained immediately and continuously. The cooling system may additionally comprise a receptacle for collecting the condensed water.

It is another aspect to provide a device as presented in any of the above, wherein the hydrophobic membrane is constructed from a material selected from one or more of a group consisting of acrylic copolymers, polytetrafluoroethylene (PTFE), polyvinylidene difluoride (PVDF), polysulfones and polycarbonates.

It is another aspect to provide a device as presented in any of the above, wherein the oxygen flow regulator is a heat/mass oxygen ($O_2$) flow meter configured for real-time flow measurement.

It is another aspect to provide a device as presented in any of the above, wherein the device additionally comprises an electronic control and display unit, comprising one or more of:

a. Unit sensors;

b. Unit controls;

c. Unit alerts; and d. Unit feedback circuits.

The control unit may be based on a designated Printed Circuit Board.

It is another aspect to provide a device as presented in any of the above, wherein the unit sensors are configured to measure at least one parameter selected from a group consisting of user set $O_2$ flow, exit $O_2$ flow, exit $O_2$ temperature, battery capacity, $H_2O_2$ reservoir level, reaction chamber pressure, and/or water tank capacity (e.g., weight).

It is another aspect to provide a device as presented in any of the above, wherein the unit control is configured to control at least one parameter selected from a group consisting of peristaltic pump RPM, cooling fan speed, and water tank drainage solenoid. The control unit may also comprise feedback circuits for one or more of the parameters as disclosed in any of the above.

It is another aspect to provide a device as presented in any of the above, wherein the control unit is configured to emit an alert in the case of one or more of:

a. low $H_2O_2$ reservoir;

b. low battery;

c. high water tank level;

d. high device pressure;

e. oxygen purity; and f. device maintenance.

It is another aspect to provide a device as presented in any of the above, in which the control unit additionally comprises a data logger, the data logger configured to record the status of the device. The control unit may be configured to communicate with an external system, the communication selected characterized as:

a. transfer recorded data to an external system;

b. receiving treatment protocol from an external system.

It is another aspect to provide a device that is powered by a battery unit, e.g., the battery may be a 12-18V/4-5 Ah Rechargeable.

It is another aspect to provide a device as presented in any of the above, wherein the device additionally comprises a Biofeedback sensor. The biofeedback sensor may be configured to detect the peripheral blood $O_2$ saturation level in the patient. The sensor may be configured to communicate with the control unit as disclosed above. For example, the sensor and the control unit may be configured to emit an alert in the case of low or high $O_2$ patient saturation levels.

It is an aspect of this disclosure to provide a method for generating oxygen, comprising steps of:
  a. combining a hydrogen peroxide solution with a catalyst;
  b. cooling the oxygen and water vapor;
  c. draining liquid water, the water condensed from the water vapor;
  d. optionally, filtering oxygen, removing water; and
  e. optionally, passing oxygen through a flow regulator.

It is another aspect to provide a method as presented in any of the above, wherein the method additionally comprises a step of controlling a flow of the hydrogen peroxide solution into a reactor.

It is another aspect to provide a method as presented in any of the above, wherein the method additionally comprises passing oxygen and water vapor through an optional catalytic filter.

It is another aspect to provide a method as presented in any of the above, wherein the step of cooling the oxygen and water vapor using a cooling and/or condensing unit, wherein the cooling is provided at least in part by generating a stream of air, the air generated by a fan, over at least a portion of the cooling and/or condensing unit.

It is another aspect to provide a method as presented in any of the above, wherein the method additionally comprises a step of analyzing the oxygen flow and temperature of oxygen exiting the cooling system.

It is another aspect to provide a method as presented in any of the above, wherein the method additionally comprises a step of alerting the user in the case of one or more of low $H_2O_2$ reservoir, low battery, high system pressure, high water tank level, oxygen purity, and/or low patient $O_2$ saturation levels.

It is another aspect to provide a method as presented in any of the above, wherein the method further comprises steps of:
  a. providing oxygen to a patient; or
  b. storing the oxygen.

It is another aspect to provide a method as presented in any of the above, wherein the method additionally comprises a step of detecting the $O_2$ saturation levels in a patient.

It is another aspect to provide a method as presented in any of the above, wherein the method additionally comprises one or more of:
  a. logging the data of the device;
  b. logging the data of the patient;
  c. transferring the data to an external system.

It is another aspect to provide a method as presented in any of the above, wherein the method additionally comprises steps of regulating the oxygen flow rate, the regulation controlled by regulating at least one parameter selected from a group consisting of flow of the hydrogen peroxide solution into a reactor and flow via the flow regulator, the flow regulation determined by at least one parameter selected from a group consisting of system pressure, reactor pressure, oxygen flow and patient $O_2$ saturation level. It is another aspect to provide a method as presented in any of the above, wherein the step of regulating the oxygen flow rate comprises a step of measuring the oxygen flow rate.

DETAILED DESCRIPTION OF THE INVENTION

Figure 1:
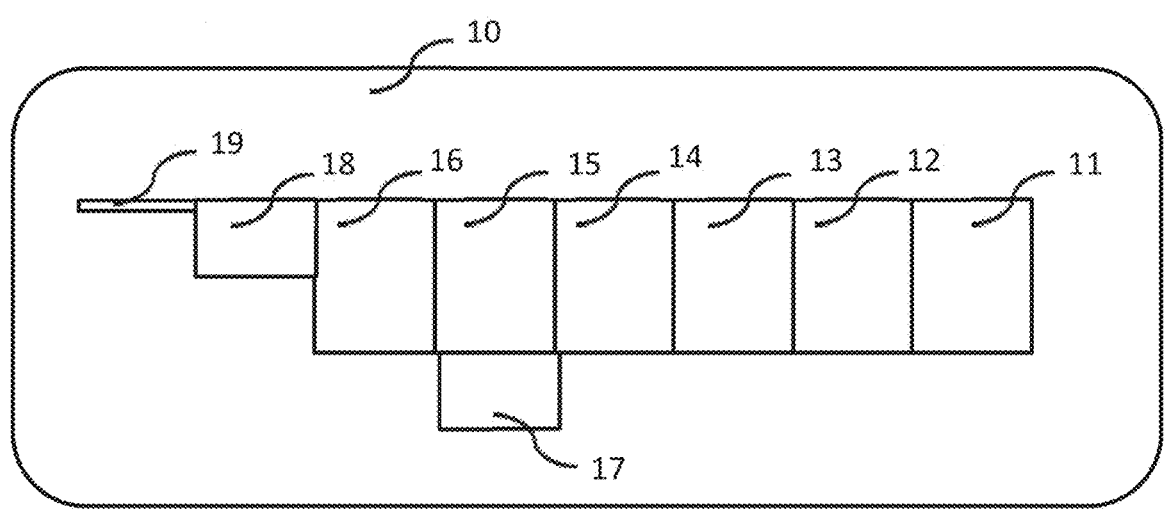
FIG. 1 is a schematic representation of the portable chemical oxygen generator according to this disclosure.

The chemical oxygen generator according to this disclosure is a device that produces oxygen though a chemical reaction. The chemical oxygen generator is important for providing emergency oxygen in situations in which other methods such as oxygen tanks or electrolysis are not feasible.

The chemical oxygen generator is used for supplementing and increasing the concentration of oxygen in the inhaled air of a patient. Such gaseous oxygen has a multitude of indications in which oxygen supplementation may be needed, including blood circulation problems (for example due to illness or due to injury), breathing problems, decreased lung function, and altitude sickness. Hypoxemia (insufficient oxygen in the blood) is a common complication in acute lower respiratory tract infections, such as pneumonia due to bacteria (*Streptococcus pneumoniae* and *Haemophilus influenzae*) and viruses (respiratory syncytial virus, influenza virus, corona virus), and is a strong risk factor for death.

Other uses can be anywhere a compact and portable oxygen generator is needed, such as in military operations, and third-world clinics. The chemical oxygen generator may also be used in submarines, aircraft, and by firefighters and mine rescue crews.

Advantageously, the chemical oxygen generator according to this disclosure is compact and portable, yet is also reliable and simple to operate. This chemical oxygen generator provides a controlled oxygen flow and temperature over an extended period of time. The flow of oxygen may be controlled by the user to dispense from 0 L/min up to about 8 L/min of oxygen gas, or up to about 10 L/min, or up to about 15 L/min.

The device can produce a sustained and controllable flow of breathable oxygen, substantially free of hydrogen peroxide and other contaminants. The term "substantially free" as used herein refers to concentrations of hydrogen peroxide or other contaminants which are below medically acceptable levels, and accordingly do not present a risk of injury or discomfort to the patient. For example, the chemical oxygen generator disclosed herein provides a flow of oxygen to the patient that has less than about 1 ppm of hydrogen peroxide, or less than about 0.5 ppm of hydrogen peroxide. In some aspects, the present device can generate a constant flow of oxygen up to about 8 L/min, or up to about 10 L/min, or up to about 15 L/min, at a temperature of less than about 40° C. for more than about 30 minutes.

Importantly, the chemical oxygen generator disclosed herein provides a flow of oxygen that is humidified and does not require the use of an external humidification apparatus. Humidified oxygen provides improved patient comfort and safety. Higher flow rates of oxygen without proper humidification may cause drying of the nasal or oral mucosa, with associated bleeding and possible airway obstruction. For patient with a nasopharyngeal catheter, an endotracheal tube or a tracheostomy, humidification of the supplied oxygen is important to keep secretions thin and to avoid mucous plugs. Endotracheal tube obstruction due to inadequate humidification of supplied oxygen has been reported as the cause of many unnecessary deaths in hospitals. The chemical oxygen generator disclosed herein addresses these concerns by suppling a flow of oxygen that is humidified.

Because the decomposition of hydrogen peroxide is highly exothermic, the oxygen produced in the reaction chamber may be at a temperature above 90° C., and up to about 98° C., and thus is too hot for dispensing to the patient. Using the chemical oxygen generator described herein, the oxygen exits the device, typically by way of flexible tubing for delivery to the patient, at a comfortably breathable temperature, i.e., below about 40° C. Advantageously, the oxygen that exits the device is not more than about 10° C. above the ambient temperature (e.g., room temperature), or is not more than about 8° C. above the ambient temperature, or is not more than about 6° C. above the ambient temperature.

The portable oxygen generating system comprises a reaction chamber, a feed system for providing and controlling hydrogen peroxide solution to the reaction chamber, and a cooling/condensing system for cooling the hot oxygen and water vapor leaving the reactor and condensing and removing water. The reaction chamber comprises a catalyst that facilitates the chemical decomposition of hydrogen peroxide to oxygen and water, an inlet for the introduction of hydrogen peroxide solution into the reaction chamber, and an outlet for the release of oxygen and water vapor from the reaction chamber. The hydrogen peroxide feed system comprises a hydrogen peroxide reservoir that contains aqueous hydrogen peroxide solution and a feed flow regulator for controlling the rate of addition of the aqueous hydrogen peroxide solution into the reaction chamber. The cooling system comprises an inlet for receiving oxygen and water vapor, a condenser comprising two or more drains, each configured to drain water condensed from the water vapor in the cooling system, and an outlet for the release of cooled oxygen gas with reduced water vapor.

Oxygen Source

The oxygen source for the chemical generation of oxygen is hydrogen peroxide, or is an adduct or complex of hydrogen peroxide. An aqueous solution of hydrogen peroxide is preferred for use as the oxygen source in the chemical reaction used in the devices provided herein.

The general reaction for the hydrogen peroxide decomposition used in the reactor to provide the formation of oxygen gas is:

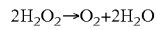

$$2H_2O_2 \rightarrow O_2 + 2H_2O$$

Hydrogen peroxide is commonly available as a water solution, with concentrations ranging from 3% up to 70%. The concentration of $H_2O_2$ is preferably at least 20%, and may be from about 30% to about 70%.

Catalyst

The reaction chamber contains a catalyst that facilitates the exothermic decomposition of hydrogen peroxide. The catalyst may comprise a metal, a metalloid, an alloy of a metal, an alloy of a metalloid, a compound of a metal, such as a metal oxide, and a compound of a metalloid, or mixtures thereof. The catalyst may comprise transition metal oxides such as $MnO_2$, $PbO_2$, $Co_3O_4$, $V_2O_5$, $KMnO_4$, silver-based catalysts, Ni-based catalysts, Fe-based catalysts, Pt-based catalysts, Pd-based catalysts. Metal catalyst may comprise one or more of silver, gold, zinc, platinum, palladium, or other metal catalyst. Alternatively, an acid may be used to catalyze the reaction.

When a solid heterogeneous catalysts in used (i.e., a catalyst that is insoluble in water), the production of oxygen occurs at the surface of the catalyst. Solid heterogeneous catalysts may be selected from the catalysts listed above and which are not soluble in water. Solid heterogeneous catalysts have the advantage that they can be reused many times with new portions of hydrogen peroxide, while maintaining high efficiency.

The catalyst may be in the form of a powder or a granulate. Catalysts in powder form may have relatively faster kinetics because of the larger surface area. However, a granulate may be more convenient to handle and to reuse. Although the high surface area of powdered catalysts helps to ensure a rapid decomposition of the hydrogen peroxide, fine powders may present issues in retaining the catalyst in the reaction chamber.

The catalyst may be in the form of a granulate, for example having a diameter of about 0.5 mm to about 5 mm. The catalyst granulate may comprise one or more of the metal, metalloid, alloy of a metal, alloy of a metalloid, a compound of a metal, or a compound of a metalloid. The granulate may further comprise one or more binder materials.

The catalyst may be dispersed or coated on the surface of a solid support material, or matrix. Alternatively, the catalyst may impregnated in in inert matrix material or binder.

The catalyst may comprise a porous matrix, for example, a porous scaffold structure onto which nano-particles of the catalyst are deposited. The porous matrix or scaffold structure can be formed from many suitable materials or combinations of materials. Non-limiting examples of suitable materials include organic materials or inorganic materials, and may include a resins, polymers, metal, glass, ceramic, activated carbon, textiles, or a combination thereof.

The porous matrix or scaffold structure may be formed of a polymer sponge. The polymer matrix/support should be selected from materials that can withstand the high concentration of hydrogen peroxide and high temperature in the reactor, and may include, for example, polycarbonates, PVC, high-density polyethylene. The porous scaffold structure may be formed by a synthesis of a poly-High Internal Phase Emulsion (poly-HIPE) method. The polymerization of the continuous phase of HIPEs leads to the formation of porous polymer monoliths, called polyHIPEs. The polyHIPEs have a high porosity with voids sizes of about 10-100 µm.

In some aspects, the porous scaffold structure may be formed by granular porous materials. For example, granules of porous material, representing a support of the porous scaffold structure, may be held together to form the porous scaffold structure. A variety of granular porous materials may be used including, but not limited to, activated carbon, polymer beads, silica sand, zirconia, alumina, anthracite, and the like.

Multiple variables may affect the oxygen release rate including the rate of addition of hydrogen peroxide, the temperature of the reaction chamber, and the amount of catalyst in contact with the hydrogen peroxide solution. The catalyst may be eliminated as a variable by ensuring that the reaction chamber contains excess catalyst relative to the hydrogen peroxide introduced into the reaction chamber. Once the reaction is under way, the temperature of the reaction chamber is maintained at or above about 90° C., and up to about 98° C., while oxygen is being produced. With a sufficient amount of solid catalyst (such as manganese dioxide) present in the reaction chamber, the rate of oxygen production may be controlled by the rate of addition of the aqueous hydrogen peroxide solution to the reaction chamber. It is therefore an aspect to produce oxygen at a controllable and selectively constant rate.

$H_2O_2$ Reservoir

A reservoir holds the hydrogen peroxide solution. The reservoir is constructed from inert, non-reactive materials such as stainless steel or polymers/plastics. The reservoir can be a single use or disposable container, or can be refillable. The reservoir may be a cartridge that holds the hydrogen peroxide solution that is fed into the reaction chamber by the feed flow regulator. In some embodiments, the reservoir is part of the system and is refiled from another container.

The reservoir can be hard or soft-sided. In some embodiments, the reservoir may be constructed like a 'syringe' i.e. is constructed from a barrel and a plunger (or piston).

In some embodiments, the reservoir is a canister capable of holding a solution of hydrogen peroxide in water that is sufficient to maintain a steady flow of oxygen for at least about 20 minutes, or at least about 30 minutes, at an oxygen flow rate of about 8 L/min, or about 10 L/min, or about 15 L/min. The concentration of hydrogen peroxide is at least about 15%, or at least about 20%. The concentration of hydrogen peroxide may be from about 30% to about 70%. The hydrogen peroxide reservoir may hold from about 500 ml to about 4000 ml of hydrogen peroxide solution, or from about 1000 ml to about 3000 ml of hydrogen peroxide solution.

Feed Flow Regulator

The rate of hydrogen peroxide solution that is provided to the reaction chamber by the feed system may be controlled by the user in order to maintain the desired oxygen flow. In some embodiments the feed flow regulator comprises, a pump to controls the flow of the hydrogen peroxide solution into the reactor. The pump may be any suitable pumping unit known in the art, including but not limited to, a displacement pump, peristaltic pump, syringe pump, piston pump, plunger pump, screw pump or reciprocating pump. In some embodiments, the reservoir may be collapsible and the feeding unit is configured to put pressure on the reservoir, thereby pushing the hydrogen peroxide solution into the reactor. In some embodiments, the feeding unit acts as a reciprocating pump with the reservoir forming part of the pump.

Reactor

The reaction chamber comprises a pressure tight housing in which occurs the chemical decomposition of the oxygen source, typically hydrogen peroxide as an aqueous solution. The reaction chamber comprises the catalyst that facilitates the chemical decomposition of hydrogen peroxide to oxygen and water, an inlet for the introduction of hydrogen peroxide solution into the reaction chamber, and an outlet for the release of oxygen and water vapor from the reaction chamber.

The reaction chamber may optionally comprise an overpressure valve to prevent a housing rupture, for example, in the event the oxygen outlet is occluded. The pressure valve may be configured to regulate the pressure in the reaction chamber by releasing excess gas and/or by regulating the feed solution flow rate. Regulation of the flow rate by the pressure valve can be conducted directly or by the control unit.

The reactor outlet may optionally comprise a filter or mesh, which functions to maintain the catalyst in the reaction chamber. Such a filter or mesh may be particularly useful in the event that the catalyst is powder and has a small particle size.

The reaction chamber is constructed from an inert, non-reactive material that can withstand temperatures of at least 100° C. The reactor may be constructed of an inert/nonreactive metal or metal alloy including aluminum, stainless steel, nickel alloys such as Inconel, and the like. Alternatively, the reaction chamber may be constructed of an inert/nonreactive polymeric material. In the present context, inert or non-reactive materials are those that do not degrade under the reaction conditions. However, in some embodiments, the material selected for the reaction chamber, and which contacts the hydrogen peroxide, may catalyze the decomposition of the hydrogen peroxide.

The aqueous hydrogen peroxide solution enters the reactor from the feeding unit through at least one aperture or inlet, such as a nozzle or a spray nozzle. The solution mixes with the catalyst, rapidly decomposing the $H_2O_2$ to $H_2O$ and $O_2$. The reaction is exothermic, reaching sustained temperatures above 90° C., and up to about 98° C., and accordingly water is vaporized to steam in the reactor. The gas produced by the decomposition of hydrogen peroxide flows out of the reactor from the reactor outlet. Optionally, the reaction chamber may also comprise a drain that allow for the removal of any accumulated liquid water. The flow of the gaseous reaction products ($O_2$, $H_2O$) out of the reaction chamber is directly proportional to the rate at which the hydrogen peroxide solution is pumped into the reactor.

Catalytic Filter

Exiting the reaction chamber are the reaction products, oxygen and water vapor, and in some embodiments, some unreacted liquid or gaseous hydrogen peroxide. In the event that some hydrogen peroxide exits the reaction chamber, the oxygen generator may optionally comprise a secondary reactor, termed a catalytic filter, that provides for the decomposition of the residual hydrogen peroxide.

The catalytic filter is constructed to decompose any hydrogen peroxide that has been vaporized or distilled by the decomposition reaction and exited the reaction chamber.

The catalytic filter contains one or more catalysts that facilitate the decomposition of hydrogen peroxide into oxygen and water, as discussed above. The catalytic filter may contain the same catalyst as the reactor or of another catalyst. The gas flow exiting the catalytic filter may be substantially free of hydrogen peroxide, and accordingly hydrogen peroxide in the exiting gas flow is at or below medically acceptable levels.

Cooling Unit/Condenser

The disclosure provides a cooling unit or system for the cooling and separating of a gaseous mixture. Although the cooling system is described for use in cooling and separating water from oxygen gas, the cooling system may be adapted for the cooling and separating of other mixtures.

The hot mixture that enters the cooling unit comprises a mixture of at least two components, a low boiling component and a high boiling component. In the case of the oxygen generator, the low boiling component is oxygen and the high boiling component is water. The hot vapor flows into the condensing/cooling unit. The condensing/cooling unit comprises an enclosure, configured to contain and cool the gas/vapor mixture, thereby converting the condensable vapor into liquid. In some embodiments, the enclosure is piping or tubing. The condensing enclosure comprises at least one drain throughout the length of the unit, and preferable a plurality of drains, enabling the condensed liquid to be separated from gas flow and drained into a tank. In some embodiments, the cooling enclosure comprises a plurality of drains, enabling draining of condensed liquid throughout the length of the cooling unit, allowing the liquid to be separated by rapid and continuously draining.

For the oxygen generator described herein, hot gasses exiting the reaction chamber or the catalytic filter, if present, are passed into a cooling unit. The gas flow entering the cooling unit may be above about 90° C., and up to about 98° C., and thus is too hot for dispensing to the patient. The cooling unit cools the gas flow to a comfortably breathable temperature, i.e., below about 40° C.

The cooling unit is configured to cool the gas flow, condensing the water vapor into liquid water, and removing the liquid water. The cooling unit allows the liquid water to be separated from the gas flow and drained into a storage tank. In some aspects, the cooling unit provides draining throughout the length of the cooling unit allowing the liquid water to be drained rapidly and continuously. This system rapidly removes the condensed water, which may be at elevated temperature, as its condensation takes place. By removing the water from the system throughout the length of the cooling enclosure, the cooling capacity of the cooling system may be directed to the efficient cooling of the oxygen gas flow, without having to fully cool the condensing water. This arrangement directs the cooling capacity of the cooling system towards cooling the lower mass oxygen flow, increasing the efficiency of the cooling.

In one embodiment, the cooling enclosure is formed of vertical sections of pipe connected by U-bends. When the device is in operation, the lower U-bends of the cooling system are horizontally situated with drainage ports at the lowest points along the pipe, allowing gravity to assist in the continuous drainage of the condensed liquid water from the cooling system. Alternatively, the cooling enclosure may comprises pipe containing the gas flow in the form of a horizontal coil, having drainage ports situated along the lowest points for each coil rotation. The cooling enclosure may be incorporated into a heat sink and/or may have cooling fins along the outside of the enclosure. A cooling fluid may be directed past the cooling enclosure to assist in the removal of heat from the cooling enclosure. The cooling fluid may be a liquid or a gas, and in some embodiments is a flow of cooling air.

In preferred aspects, the cooling system is an active air cooling system. An electric fan may be used as the active component of the cooling system. The cooling air is generated by the fan passes and around the enclosure, cooling the body of the enclosure. Cooled oxygen exits condensing enclosure via the exhaust/exit tube. Advantageously, the oxygen that exits the cooling system is not more than about 10° C. above the ambient temperature, or is not more than about 8° C. above the ambient temperature, or is not more than about 6° C. above the ambient temperature.

Hydrophobic Membrane

In embodiments, humid oxygen gas exiting the cooling system passes through a hydrophobic membrane, filtering traces of water. Liquid water can interfere with the accuracy of measuring the oxygen flow. The hydrophobic membrane is a microporous membrane of polymeric material. The hydrophobic membrane may be constructed from any material known in the art for this purpose, including acrylic co-polymers, polytetrafluoroethylene (PTFE), polyvinylidenedifluoride (PVDF), polysulfones and polycarbonates. Commercially available as ventilation plugs having a hydrophobic membrane may be used for this purpose.

In embodiments, a drier may be situated between the reaction chamber, or the catalytic filter if present, and the cooling system. The drier comprises a hydrophobic membrane and serves to remove a portion of the water from the gas flow prior to the flow entering the cooling system. The drier may remove up to about 90% of the water from the gas flow, or from about 70% to about 90% of the water from the gas flow. Removing a portion of the water prior to the gas flow entering the cooling system may increase the efficiency of the cooling system. The hydrophobic membrane is a microporous membrane of polymeric material and may be constructed from any material known in the art for this purpose, including acrylic co-polymers, polytetrafluoroethylene (PTFE), polyvinylidenedifluoride (PVDF).

FIG. 1 schematically shows the basic unit 10 of an embodiment of the chemical oxygen generator. The reservoir 11 holds the hydrogen peroxide solution. The holder can be single use or refillable. In some embodiments, the reservoir is a cartridge that holds the solution and is fed into the system. In some embodiments, the reservoir is part of the system and is refilled from another container. The reservoir can be hard or soft-sided. The reservoir is constructed from inert, non-reactive, medicinal grade materials. In some embodiments, the reservoir is constricted like a 'syringe' i.e. is constructed from a barrel and a plunger (or piston). In some embodiments the reservoir is a canister capable of holding a solution of hydrogen peroxide ($H_2O_2$) in water. The percentage of hydrogen peroxide is at least 20% and in some embodiments is 30-70%.

The feeding unit 12 controls the flow of the hydrogen peroxide solution into the reactor. In some embodiments, the feeding unit is a pump. The pump can be, for example, a displacement pump, peristaltic pump, syringe pump, piston pump, plunger pump, screw pump or reciprocating pump. In some embodiments, the reservoir 12 is collapsible and the feeding unit is configured to put pressure on the reservoir, pushing the hydrogen peroxide solution into the reactor. In some embodiments, the feeding unit acts as a reciprocating pump with the reservoir forming part of the pump.

The feeding unit can be set to control the flow rate according to various parameters including: hydrogen peroxide solution flow rate, oxygen flow rate (at the exit of the device), and reaction chamber pressure. In some embodiments, the feeding unit additionally comprises a pressure sensor.

The reaction chamber 13 comprises the catalyst that facilitates the chemical decomposition of hydrogen peroxide to oxygen and water, an inlet for the introduction of hydrogen peroxide solution into the reaction chamber, and an outlet for the release of oxygen and water vapor from the reaction chamber. The reaction chamber is constructed from an inert, non-reactive material that can withstand temperatures of at least 100° C.

The aqueous hydrogen peroxide solution enters the reactor from the feeding unit through at least one aperture or inlet, such as a nozzle or a spray nozzle. The reactor contains the catalyst that catalyzes the decomposition of hydrogen peroxide to water and oxygen. The solution mixes with the solid catalyst particles, decomposing the hydrogen peroxide to $H_2O$ and $O_2$. The reaction is exothermic, reaching temperatures above 90, and up to about 98° C. The gas produced by the decomposition of hydrogen peroxide flows out of the reactor and through the catalytic filter 14.

The reaction chamber can additionally comprise a pressure valve. In some embodiments the pressure valve is configured to regulate the pressure in the reaction chamber by releasing excess gas or by regulating the solution flow rate. Regulation of the flow rate by the pressure valve can be conducted directly or by the control unit.

The catalytic filter 14 is constructed to decompose any hydrogen peroxide that has been vaporized or distilled by the decomposition reaction. The filter can be constructed of the same catalyst as present in the reactor or of another catalyst.

Gas that flows through the filter 14 passes into a cooling unit 15. The cooling unit is configured to cool the gas, condensing the water vapor into liquid water. The cooling unit enables the liquid to be drained into a tank. In some embodiments, the cooling unit provide draining throughout the length of the cooling unit. In some embodiments, the liquid is drained instantly and continuously. The water tank holds the water and can be drained.

Gas that passes through the cooling unit 15 passes through a hydrophobic membrane (or filter) 16 to remove any water vapor that was not condensed throughout the cooling unit.

An oxygen flow regulator 17 comprises a flow meter that measures the amount of oxygen that passes the filter 16. The flow meter may regulate the feeding unit to ensure that the flow of oxygen is continuous and at the required level. The flow regulator can also measure the temperature of the gas to make sure that the oxygen is not too hot for the patient. In some embodiments, the flow regulator additionally comprises a valve for regulating the oxygen flow. The valve can be manual, mechanical or electro-mechanical. In some embodiments the valve is controlled by the user, the control unit or directly by the flow meter.

The system contains a Control and Display unit and power source 18. A display unit can display all of the critical device parameters: oxygen flow, oxygen temperature, water tank content level, reservoir level, system pressure, battery power level etc. The control and display unit can also track the overall status of the system, such as usage status, catalyst status, maintenance etc.

In some embodiments, the system additionally comprises a biosensor. In some embodiments, the biosensor is an $O_2$ blood saturation sensor that is connected to a patient. The sensor can be connected to the control unit to track the saturation level of the patient. In some embodiments, the control unit is configured to control the Oxygen flow rate according to the $O_2$ saturation level of the patient. The control unit can control the oxygen rate by regulating the exit valve or the feeding unit.

The system contains an exit port 19 through which the final oxygen produced exits the device and can then be delivered to a patient or stored for later use.

Figure 2:
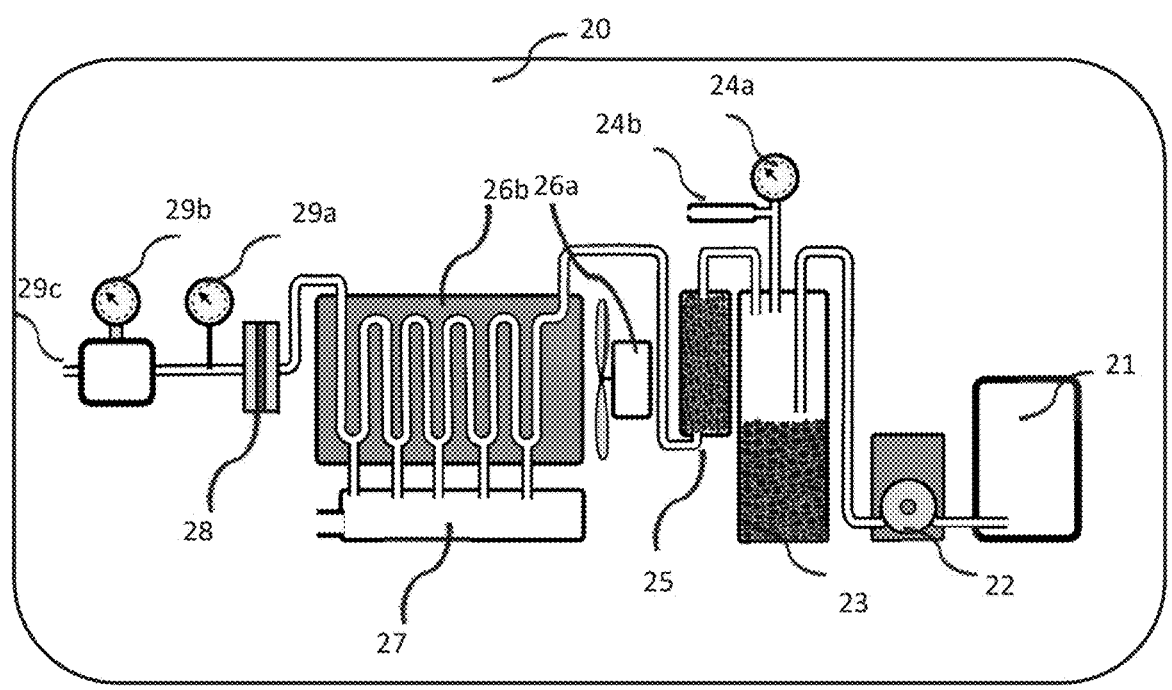
FIG. 2 depicts an embodiment of the portable chemical oxygen generator according to the present disclosure.

Reference is now made to FIG. 2, which depicts a specific embodiment of the oxygen generating device.

The oxygen generating device 20, comprises a hydrogen peroxide cartridge 21 containing the hydrogen peroxide solution (for example 50%-60%), which is the substrate of the chemical reaction, producing $H_2O$ and $O_2$. The cartridge volume may be 750-3000 ml, sufficient to produce a flow of 10 L/min $O_2$ for 30-45 min. The cartridge is designed to be rapidly replaceable once it gets empty, enabling continues flow of oxygen.

A pump 22, such as peristaltic pump, drives the hydrogen peroxide solution from the cartridge 21 to the reaction chamber 23, where the chemical reaction takes place. The pump speed (RPM) is controlled through the control unit.

The hydrogen peroxide is fed into the reaction chamber 23, mixing with the solid catalyst particles, and decomposing the hydrogen peroxide to water and oxygen. The reaction is exothermic, reaching temperatures above about 90° C., and up to 98° C., and creating a constant Power up to 1,500 W.

Exiting the reaction chamber are oxygen, water as steam, and some liquid and gaseous hydrogen peroxide. The flow of the reaction products ($O_2$, $H_2O$) is directly proportional to the pump RPM (the reaction is saturated with catalyst). A pressure gauge 24a tracks the pressure in the reaction chamber. In cases of excess pressure, a pressure valve 24b can release excess gas.

The mixture exiting the reaction chamber is directed into a catalytic filter 25, packed with catalytic particles. Traces of hydrogen peroxide (liquid or gaseous) are chemically decomposed to oxygen and water, preventing any corrosive hydrogen peroxide from reaching the patient.

The hot oxygen and steam exiting the catalytic filter 25 flows into an active air cooling system comprising a fan 26a and a cooling enclosure 26b. While going through the system, condensation takes place, water is pouring down through ports at the bottom of each curve within the cooling enclosure. This arrangement efficiently directs the cooling capacity towards low mass steam condensation, rather than cooling high mass water. An electric fan 26b (60 W) is used as the active component of the cooling system.

Water is collected into a water tank 27, and drained out timely through a solenoid controlled tap.

Humid oxygen exiting the cooling system flows through a hydrophobic membrane 28, filtering additional water. Liquid within the $O_2$ pipe can interfere with accurately measuring the $O_2$ flow.

A heat meter 29a and mass oxygen flow meter 29b are used for real-time flow measurement of the oxygen exiting the device through exit port 29c.

Figure 3:
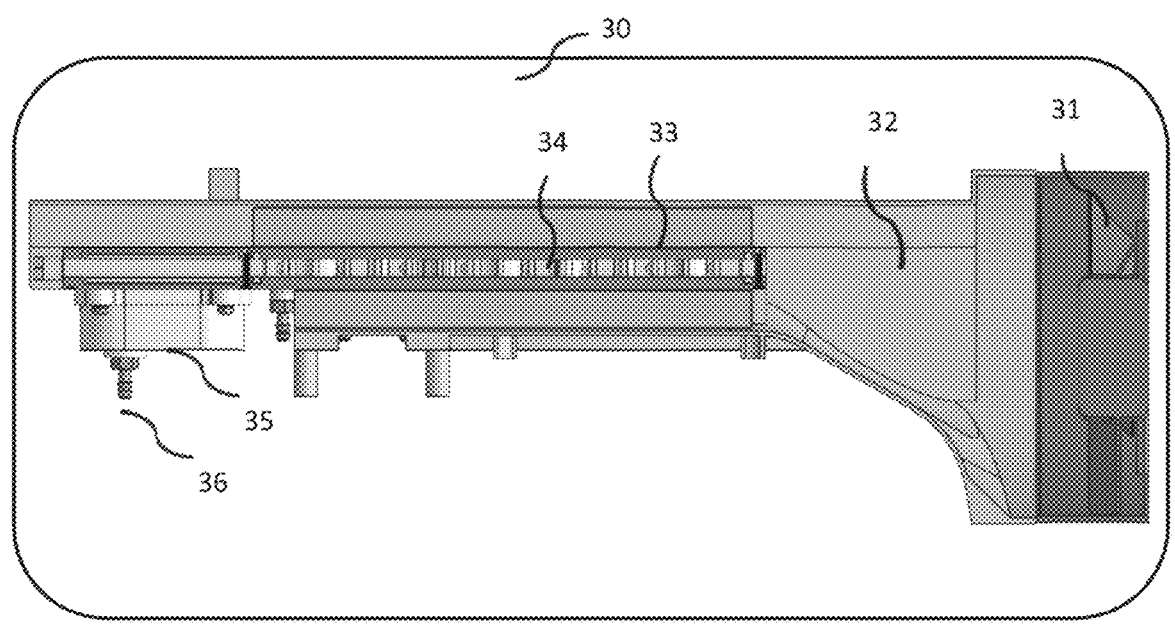
FIG. 3 depicts an embodiment of the cooling system according to this disclosure.

Reference is now made to FIG. 3, providing a cross-section of a cooling system 30. The cooling air is generated by a fan 31 and funneled 32 to an area 33 surrounding the pipe 34 containing the oxygen and water vapor generated by the reactor. The gas stream is then de-humidified by a hydrophobic membrane 35 before exiting the system through port 36, to be provided to a patient.

Figure 4:
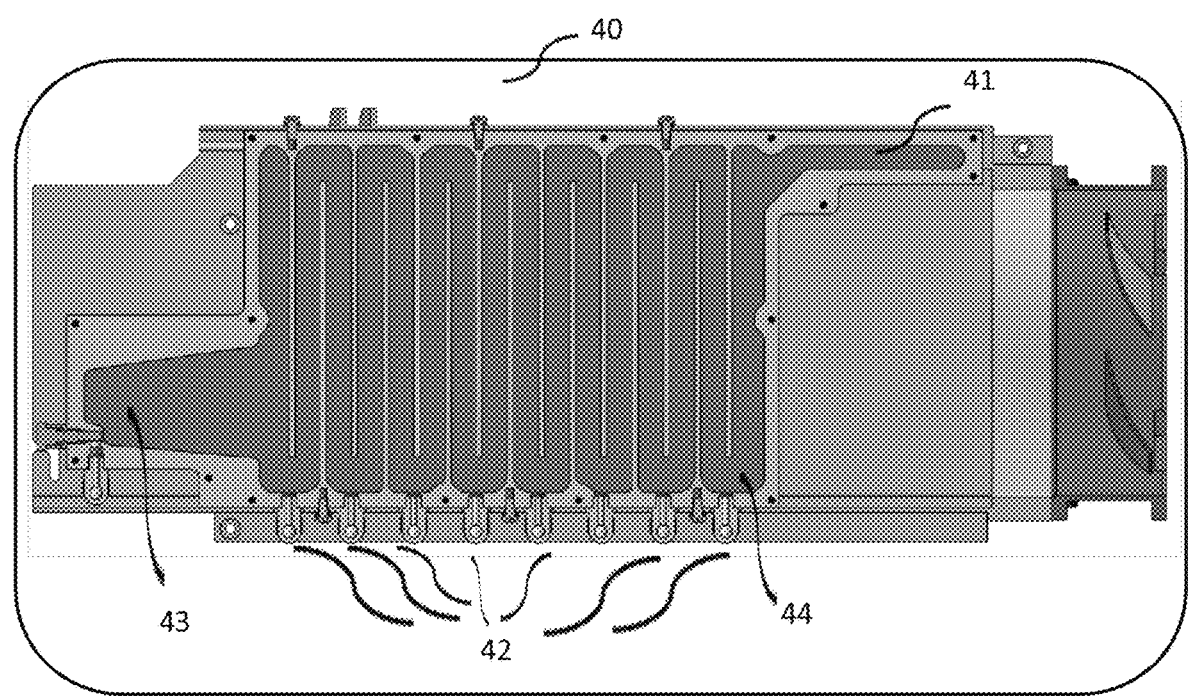
FIG. 4 depicts an embodiment of the heat sink system according to this disclosure.

Reference is now made to FIG. 4 describing a heat sink cooling system 40. The mixture of hot oxygen and water vapor enters the sink through 41. As the gas is cooled, and the water vapor is converted to liquid, the liquid water is drained through the drainage ports 42 at the lowest position of the U-bends 44, such that the content of water in the oxygen that exits the system through 43 is reduced. FIG. 4 presents the cooling unit of FIG. 3 at a 90° rotation on the Y-axis (i.e., a side view).

Figure 5A:
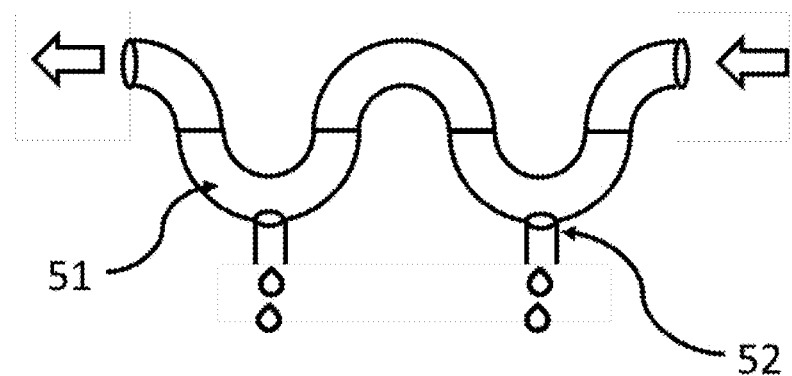
FIG. 5A shows an embodiment of the cooling enclosure that comprises consecutive U-bends having drainage ports at the lower portion of each lower U-bend for the drainage of liquid (water) that has condensed in the cooling enclosure.
Figure 5B:
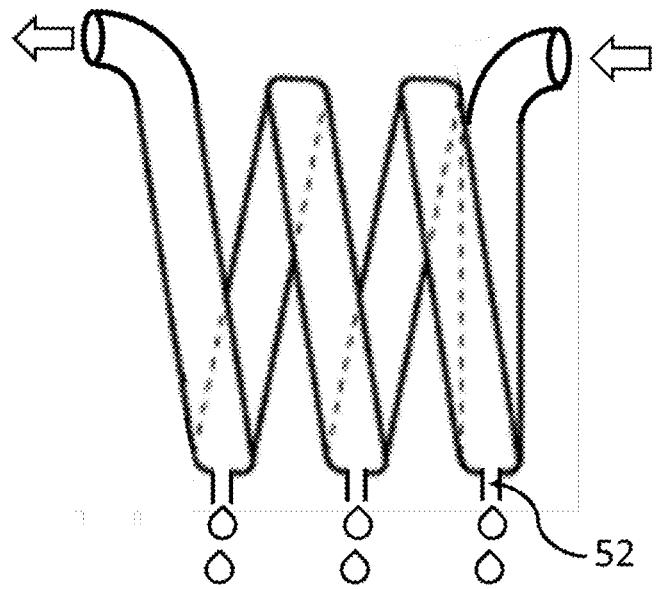
FIG. 5B shows an embodiment of the cooling enclosure that comprises a horizontal coil-shaped cooling enclosure, in which the drainage ports are situated at the lowest portion of each coil rotation.

Reference is now made to FIG. 5, which shows representative embodiment of the cooling enclosure of the cooling system. FIG. 5A shows a cooling enclosure that comprises consecutive U-bends. At the lowest portion of each lower U-bend 51, there is a drainage port 52 for the drainage of liquid (water) that has condensed in the cooling enclosure. FIG. 5B shows a horizontal coil-shaped cooling enclosure, in which the drainage ports 52 are situated at the lowest portion of each coil rotation.

Figure 6:
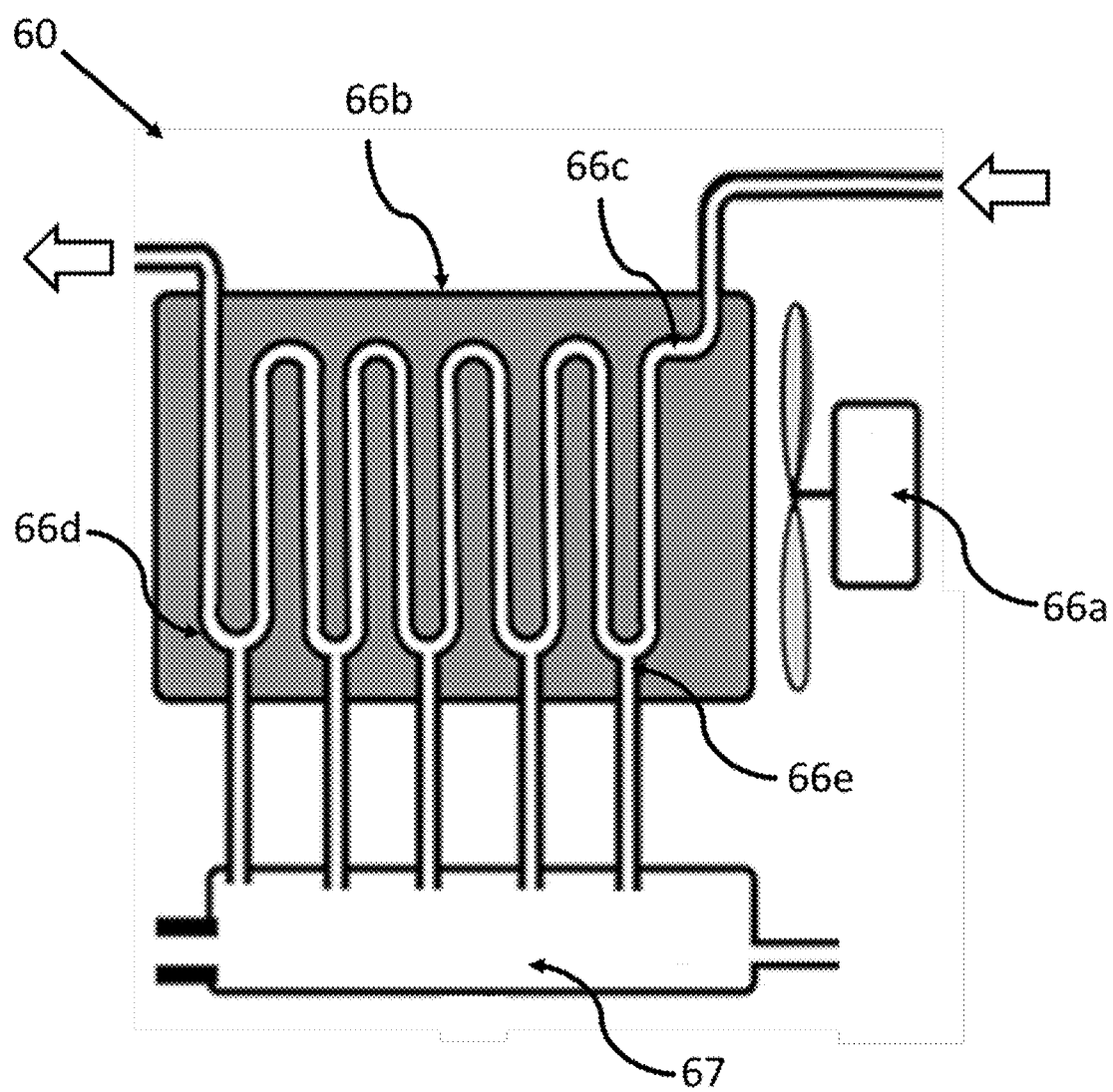
FIG. 6 depicts an embodiment of the cooling system according to this disclosure.

Reference is now made to FIG. 6, which shows a representative embodiment of the cooling system. The hot gaseous mixture, (such as hot oxygen and steam) flows into an active air cooling system 60 comprising a fan 66a and a cooling enclosure 66b. While going through the system, condensation takes place, the lower boiling component (such as water) condenses and drains down through the drainage ports 66e at the bottom of each lower U-bend 66d within the cooling enclosure. This arrangement efficiently directs the cooling capacity towards a reduced mass stream comprising the lower boing component (such as oxygen), rather than cooling high mass of the condensed higher boiling component (such as water). An electric fan 66b is used as the active component of the cooling system. The higher boiling component (such as water) is collected into a tank 67.

Figure 7:
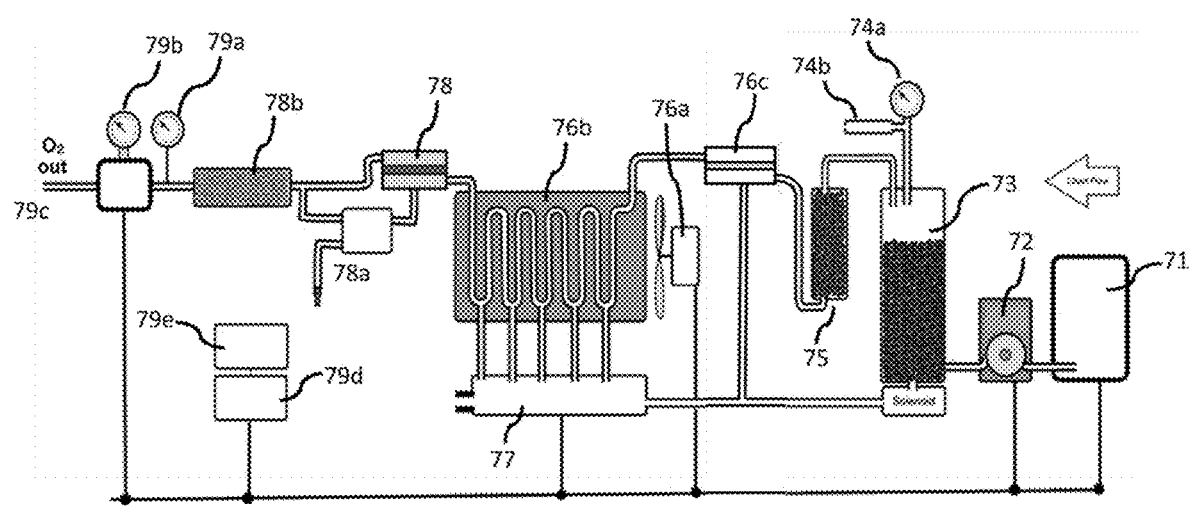
FIG. 7 depicts an embodiment of the portable chemical oxygen generator according to the present disclosure.

Reference is now made to FIG. 7, which depicts a specific embodiment of the oxygen generating device. The oxygen generating device 70, comprises a hydrogen peroxide cartridge 71 containing the hydrogen peroxide solution (for example 50%-60%), which is the substrate of the chemical reaction, producing $H_2O$ and $O_2$. The cartridge volume may be 750-3000 ml, sufficient to produce a flow of 10 l/min $O_2$ or more for 30-45 min. The cartridge is designed to be instantly replaceable once it gets empty, enabling continues flow of oxygen.

A pump 72, such as peristaltic pump, drives the hydrogen peroxide solution from the cartridge 71 to the reaction chamber 73, where the chemical reaction takes place. The pump speed (RPM) is controlled through the control unit 79d.

The hydrogen peroxide is fed into the reaction chamber 73, mixing with the solid catalyst particles, and decomposing the hydrogen peroxide to water and oxygen. The reaction is exothermic, reaching temperatures above about 90° C., and up to 98° C.

Exiting the reaction chamber are oxygen, water as steam, and some liquid and gaseous hydrogen peroxide. The flow of the reaction products ($O_2$, $H_2O$) is directly proportional to the pump RPM (the reaction is saturated with catalyst). A pressure gauge 74a tracks the pressure in the reaction chamber. In cases of excess pressure, a pressure valve 74b can release excess gas.

The mixture exiting the reaction chamber is directed into a catalytic filter 75, packed with catalytic particles. Traces of hydrogen peroxide (liquid or gaseous) are chemically decomposed to oxygen and water, preventing any corrosive hydrogen peroxide from reaching the patient.

The hot oxygen and steam exiting the catalytic filter 75 flows into a drier 76c which comprises a hydrophobic membrane and serves to remove a portion of the water from the gas flow prior to the flow entering the cooling system.

The partially dried hot oxygen and water vapor flows into an active air cooling system comprising a fan 76a and a cooling enclosure 76b. While going through the system, condensation takes place and liquid water drains down through the drainage ports at the bottom of each lower U-bend within the cooling enclosure. The water is collected into a water tank 77, and drained out through a solenoid controlled tap.

Liquid within the $O_2$ pipe can interfere with accurately measuring the $O_2$ flow. Humid oxygen exiting the cooling system flows through a hydrophobic membrane 78, filtering additional water. Any water may be drained from the hydrophobic membrane through the drainage 78a. Optionally, the oxygen flow exiting the hydrophobic filter passes through an additional drying filter 78b comprising a desiccating agent such as silica.

A temperature gauge 79a and mass oxygen flow meter 79b are used for real-time flow measurement of the oxygen exiting the device through exit port 79c.

The device is powered by a battery unit 79e, which may comprise a rechargeable 12-18V/4-5 Ah battery. The device additionally comprises an electronic control and display unit 79d. The control and display unit 79d may be configured to control parameters selected from pump RPM, cooling fan speed, and water tank drainage. The control unit may also comprise feedback circuits for one or more of the parameters as disclosed in any of the above. The control unit may be configured to monitor and/or emit an alert in the case of one or more of low $H_2O_2$ reservoir, low battery, high water tank level, high device pressure, oxygen purity, and device maintenance.

EXAMPLES

Materials and Methods

The cooling system performance was tested by several parameters: drained liquid mass and volume, drained liquid temperature and the heat released from each outlet point.

The data was collected during operation of the device for 5 minutes using 50% of hydrogen peroxide ($H_2O_2$) and a catalyst for hydrogen peroxide decomposition (Hydrogen Link OxyCatalyst). The gas flow was measured by a gas flow meter and was controlled indirectly, by controlling the hydrogen peroxide flow using a peristaltic pump.

The volume was measured by measuring cylinders, the mass was measured by an analytic balance. The temperature was measured by a thermometer (ExTech 4-channel thermometer, model SDL 200). The heat was calculated using the equation:

$$Q = m \cdot Cp \cdot (T_{inlet} - T_{outlet})$$

Q=heat (cal.)
m=drained liquid mass (g)

$$Cp = \text{heat capacity of water} \left(\frac{cal}{g \cdot ° C.}\right)$$

T=drained liquid temperature (° C.)
$T_{inlet}$=reaction temperature, for the first outlet point;
$T_{outlet}$ of the previous outlet point, for n>2 outlet point
Table 1 provides the parameters measured at the cooling system of the oxygen generator.

TABLE 1

| Catalyst Mass | Gas Flow | Reaction Temp (° C.) | | Vol. (ml) | Mass (g) | Liquid Temp (° C.) | Gas Temp (° C.) | Heat Release (cal) |
|---|---|---|---|---|---|---|---|---|
| 272 g | 10 LPM | 92.4 | outlet 1 | 131 | 126.83 | 60.5 | 23.8 | 4045.877 |
| | | | outlet 2 | 71 | 68.68 | 50.7 | 25.4 | 432.684 |
| | | | outlet 3 | 21 | 19.75 | 40 | 24.7 | 211.325 |
| | | | outlet 4 | | 1.62 | 24.4 | 23.5 | 25.272 |
| 136 g | 10 LPM | 92.4 | outlet 1 | 180 | 175.47 | 60.6 | 25.3 | 5579.946 |
| | | | outlet 2 | 69 | 66.63 | 55.9 | 23.9 | 313.161 |
| | | | outlet 3 | 9.1 | 8.84 | 36.9 | 24.5 | 167.96 |
| | | | outlet 4 | 0 | 0 | | | |
| 272 g | 7 LPM | 96.1 | outlet 1 | 112 | 108.48 | 57 | 22.7 | 4339.2 |
| | | | outlet 2 | 24 | 22.46 | 38.8 | 23.5 | 487.382 |
| | | | outlet 3 | 3.7 | 3.14 | 27.7 | 24.2 | 34.854 |
| | | | outlet 4 | 0 | 0 | | | |
| 136 g | 7 LPM | 95.1 | outlet 1 | 66 | 63.81 | 56.1 | 22.4 | 2488.59 |
| | | | outlet 2 | 44 | 42.04 | 52.4 | 22.35 | 155.548 |
| | | | outlet 3 | 4.8 | 4.4 | 32.1 | 22.6 | 89.32 |
| | | | outlet 4 | 0 | 0 | | | |
| 272 g | 5 LPM | 92.4 | outlet 1 | 118 | 114.4 | 38.1 | 20.6 | 6211.92 |
| | | | outlet 2 | 15 | 14.2086 | 25.7 | 20.9 | 176.18664 |
| | | | outlet 3 | | 0.2 | 20 | 22.4 | 1.14 |
| | | | outlet 4 | 0 | 0 | | | |
| 136 g | 5 LPM | 92.4 | outlet 1 | 85 | 82.9 | 45.8 | 22.7 | 3863.14 |
| | | | outlet 2 | 19 | 17.68 | 27.7 | 22.3 | 320.008 |
| | | | outlet 3 | 0 | 0 | | | |
| | | | outlet 4 | 0 | 0 | | | |

1.1 Effect of Gas Flow

Theoretically, increasing the gas flow requires increasing the hydrogen peroxide flow, which increases its decomposition reaction rate in the reaction chamber. Adding more reactants, hydrogen peroxide in this case, encourages the catalyst to catalyze the decomposition reaction. That leads to the production of more oxygen and water and increases the temperature in the reaction chamber due to the production of heat from the exothermic reaction. Thus, as the hydrogen peroxide flow increases and the amount of hydrogen peroxide entering the reaction chamber increases, it is expected that the drained liquid mass and liquid temperature will increase as more heat is released.

1.1.1 Drained Liquid Mass

The products of the hydrogen peroxide decomposition reaction are water and oxygen. In the high flow experiments (7 and 10 LPM), traces of hydrogen peroxide were found in the drained liquid at the first and the second outlet points. That indicates that not all the $H_2O_2$ reacted in the reaction chamber and it was condensed in the cooling system. It can be concluded that the amount of catalyst is to be increased to compensate for the high flow of the $H_2O_2$.

Figure 8:
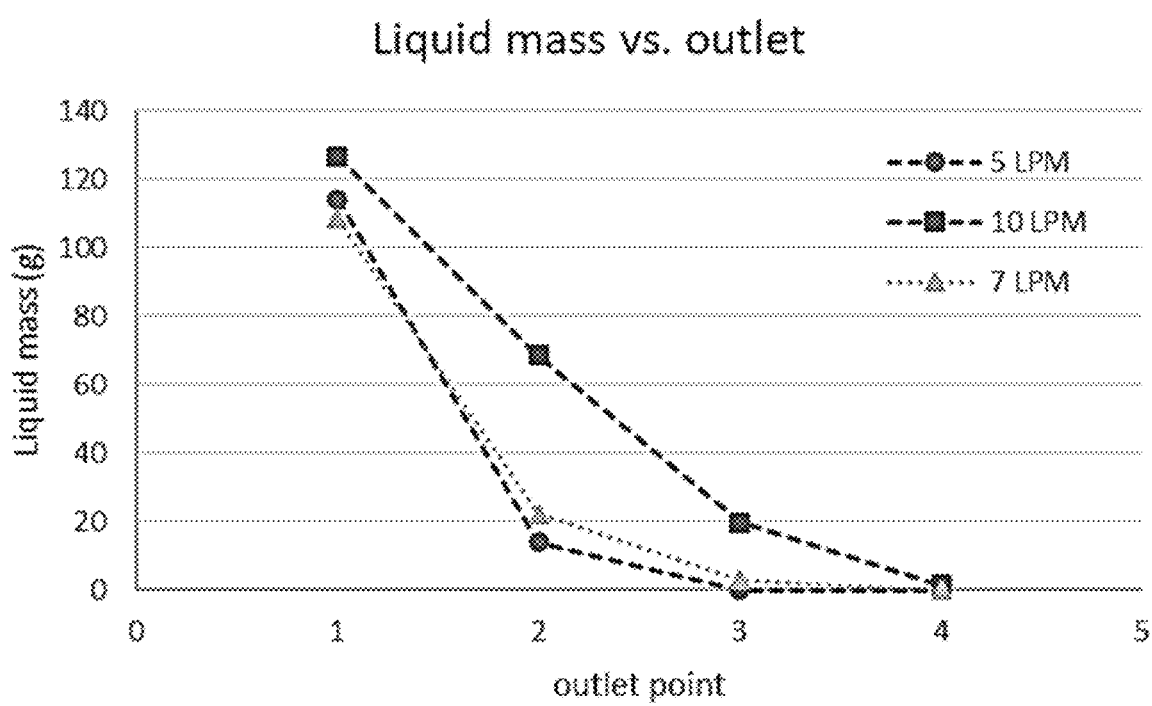
FIG. 8 shows the influence of the gas flow on the drained liquid from each outlet.

FIG. 8 presents the liquid mass drained from the outlet points 1-4 at 5, 7 and 10 LPM flow. As it can be seen, only for the high flow of 10 LPM the 4th outlet point participated in the cooling process. In addition, the trend is the same for all three flows. The drained liquid mass decreases as the outlet point number increases. That can be explained by the fact that most of the liquid is condensed in the first outlet point due to the high temperature difference (the gas stream has a temperature of 92-96° C. as it goes out from the reaction chamber).

The graph of the 10 LPM is higher than the two others in a significant manner, while the difference between the 5 and the 7 LPM is small. However, for the 7 LPM, higher total mass of liquid was drained from the cooling system (not significantly). Moreover, for the 7 LPM, the 3rd outlet point participated in the cooling process while for the 5 LPM only 2 outlet points were needed.

1.1.2 Drained Liquid Temperature

The temperature of the drained liquid indicates the efficiency of the cooling process at each outlet point. As presented in FIG. 9, for all three flow rates, the temperature decreases as the outlet point number increases. Comparison between the different flows shows that at each outlet point the temperature decreases with the flow. The efficiency is the highest for the 5 LPM and the lowest efficiency was obtained for the 10 LPM. For the highest flow, the highest mass of products (water and oxygen) was produced. Thus, the cooling needed is "harder". It is expressed by higher temperature of the drained liquid and the numbers of outlet points needed for the cooling.

1.1.3 Heat Release

Figure 9:
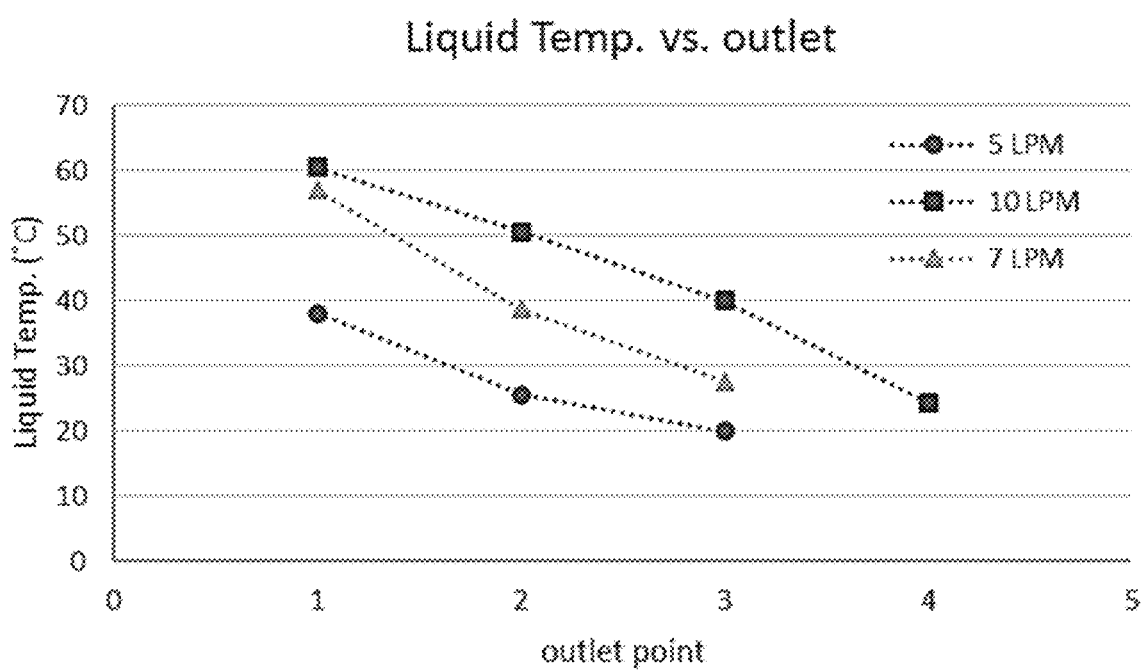
FIG. 9 shows the influence of the gas flow on the temperature of the drained liquid.
Figure 10:
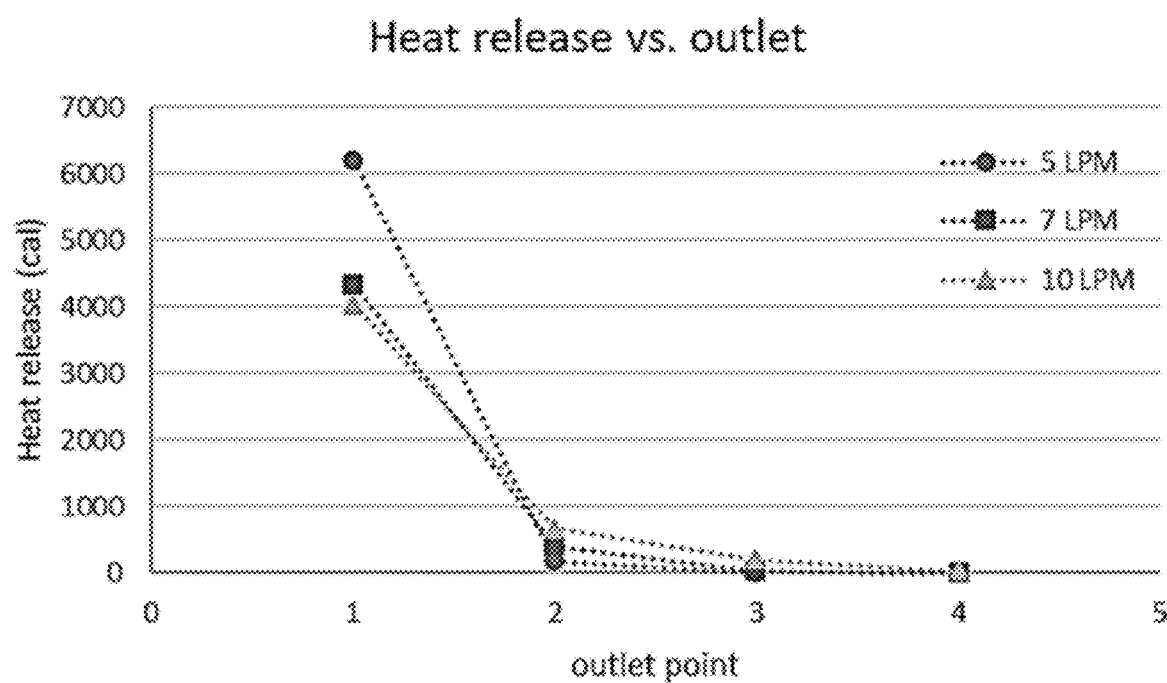
FIG. 10 shows the influence of the gas flow on the heat released by the cooling system.

The heat released during the cooling process is calculated based on the drained liquid mass and the temperatures difference between the inlet and the outlet. This parameter, as the temperature, indicated the efficiency of the cooling. FIG. 10 shows the heat released from each outlet point at the different flows. The heat released at each outlet point decreases as the point number increases since less mass is required to be cooled and the delta of the temperature gets smaller, so there is less heat to release. This trend exists in all tested flows. The lowest flow of 5 LPM required the lowest hydrogen peroxide flow. Low flow of reactant enabled the catalyst to more fully catalyze the hydrogen peroxide than in the other gas flow experiments and enabled the cooling system to evacuate more of the heat at the beginning of the cooling system. The high flow of hydrogen peroxide (as in the 7 and 10 LPM experiments) cause an increase of high temperature gas to be cooled, thus the efficiency of the cooling is lower which is expressed in higher liquid temperature as shown in FIG. 9 and lower heat released presented in FIG. 10.

1.2 Effect of Catalyst Amount

In general, chemical reactions occur faster in the presence of a catalyst because the catalyst provides an alternative reaction pathway with a lower activation energy than the non-catalyzed mechanism. Thus, the catalyst amount has a significant influence upon the reaction rate. It is expected to get a higher reaction rate for higher amount of catalyst up to the point that the catalyst is present in sufficient excess.

1.2.1 Drained Liquid Mass

Figure 11:
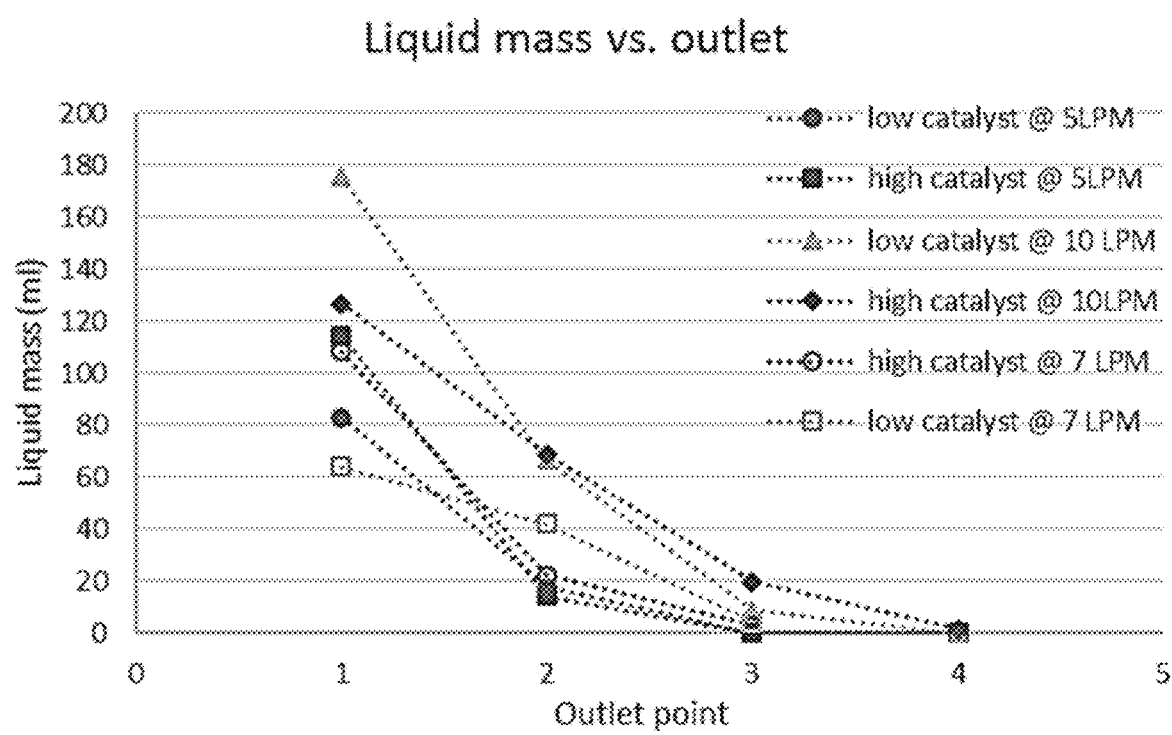
FIG. 11 shows the influence of the gas flow and the catalyst amount on the drained liquid.

FIG. 11 presents the influence of the catalyst amount on the drained liquid for different flows. In order to obtain a certain gas flow for the same liquid flow (constant pump voltage) longer time was needed in the low catalyst experiments (30 seconds in all low catalyst experiments). Because the overall experiment time was constant (5 minutes), less drained liquid was obtained during that time from the first outlet point. For the second and the third outlets the trend was opposite since less liquid was left to be condensed (most of the liquid was condensed at the first outlet point). However, for high flow of 10 LPM, for the low catalyst amount, higher mass of liquid was drained from all the outlets points compared to the high amount. That can be explained by the "overloading phenomenon" that was observed in the high flow experiment. As been explained in section 1.1.1, 10 LPM was found to be too high flow for that reaction chamber design. That causes to an overloading the reaction chamber with hydrogen peroxide while the catalyst cannot catalyze it on the same rate. The result of the "overloading phenomenon" is incomplete reaction and presence of hydrogen peroxide in the drained liquid. That phenomenon is stronger for the high flow (10 LPM) low catalyst experiment. It means that more hydrogen peroxide is drained than compared to the high catalyst experiments. Since hydrogen peroxide is denser than water, the drained liquid mass for the low catalyst amount is higher.

1.2.2 Drained Liquid Temperature

Figure 12:
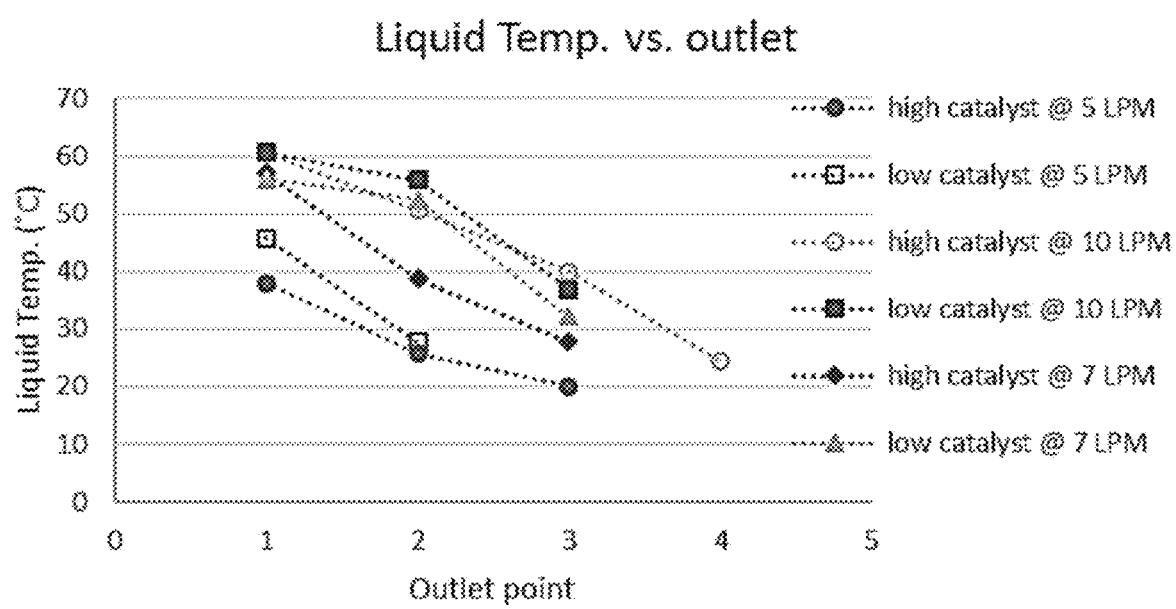
FIG. 12 shows the influence of the gas flow and the catalyst amount on the drained liquid temperature.

The results for the temperature are presented in FIG. 12 and shows dominant behavior—the higher temperatures obtained for the lower catalyst amount for a certain flow. That is expected since the mass of drained liquid is lower. That means less energy is released through the condensing process, and it leads to higher temperatures. However, the 10 LPM shows not consistent behavior. For the first outlet point the low catalyst has almost the same liquid drained temperature, for the second outlet the low catalyst has higher liquid drained temperature and for the third one the high catalyst caused to higher temperature. Again, the overloading prevented from some of the hydrogen peroxide to react in the reaction chamber, and it is reasonable to assume that some of the reaction occurred in the cooling system, thus no conclusions can be made based on the temperature results.

Comparing the different flows can show that decreasing the flow, decreases the temperature at each outlet point, for each catalyst amount, since more liquid was condensed and by that consumed more of the released heat for the condensing process which is an endothermic.

1.2.3 Heat Release

Figure 13:
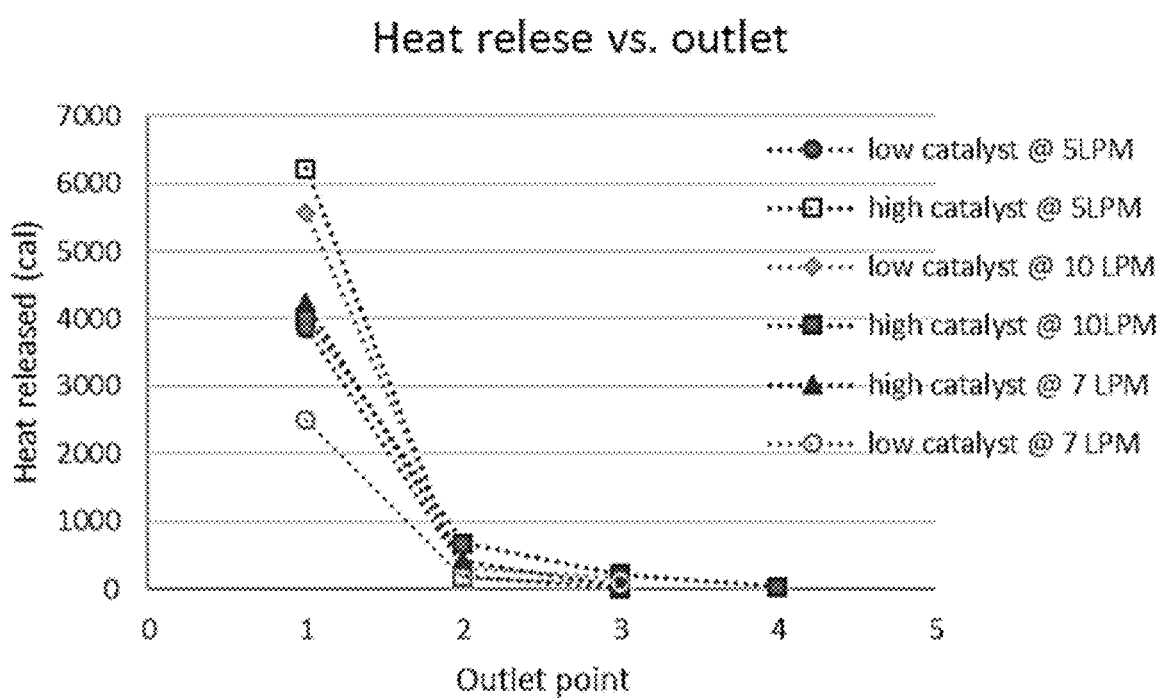
FIG. 13 shows the influence of the gas flow and the catalyst amount on the heat release.

Looking at the heat release results presented in FIG. 13 show that increasing the flow decreases the heat released from each outlet for each catalyst amount (except for the 10 LPM which, as being explained, was overloaded). High heat released by the cooling system represent the efficiency of the cooling process. The best efficiency was obtained for the lower flow at each catalyst amount since the delta of the inlet and outlet temperatures was the biggest. Based on the Equation 1, the heat is calculated based on this temperatures difference. The trend for all the experiments is the same— the heat released from each outlet point decreases dramatically between the first and the second outlet points and the slope becomes more moderate between the second and the third outlets. This result proves that most of the heat releases in the first outlet point and it is the most efficient cooling point.

Comparing between two catalyst amounts for the same flow (except the 10 LPM) reveals that for the higher catalyst amount the more heat release due to the fact that higher amount catalyze the reaction better so higher mass of products is obtained (while the pump voltage is constant) during the experiment and higher heat is generated in this exothermic reaction.

The results show that the drained liquid mass decreases as the outlet point number increases. For each flow rate, the drained liquid temperature decreases as the outlet point number increases. At each outlet point, the temperature also decreases with the flow. The heat released at each outlet point decreases as the point number increases. For the highest flow rate, the highest mass of products (water and oxygen) was produced.

The efficiency is the highest for the 5 LPM and the lowest efficiency was obtained for the 10 LPM. The best efficiency was obtained for the lower flow at each catalyst amount. The first outlet point is the most efficient cooling point.

We claim:
1. A portable oxygen generating device, comprising:
   a reaction chamber comprising:
      a catalyst that facilitates the chemical decomposition of hydrogen peroxide to oxygen and water,
      an inlet for introduction of hydrogen peroxide solution into the reaction chamber, and
      an outlet for release of oxygen and water vapor from the reaction chamber;
   a hydrogen peroxide feed system in fluid communication with the inlet of the reaction chamber, comprising:
      a hydrogen peroxide reservoir that contains aqueous hydrogen peroxide solution as a replaceable cartridge, and
      a feed flow regulator that controls a rate of addition of the aqueous hydrogen peroxide solution into the reaction chamber;
   a cooling system, comprising:
      an inlet, in fluid communication with the outlet of the reaction chamber, for receiving the oxygen and water vapor, and
      a condenser comprising two or more drains, each configured to drain water condensed from the water vapor in the cooling system;
      an outlet for release of cooled oxygen gas with reduced water vapor; and
   a catalytic filter situated in fluid communication between the outlet of the reaction chamber and the inlet of the cooling system, wherein the catalytic filter comprises a catalyst for the decomposition of hydrogen peroxide to oxygen and water; and
   an electronic control unit that regulates a flow rate of oxygen from the device.

2. The device of claim 1, wherein the device additionally comprises one or more hydrophobic membranes situated after the cooling system, or situated between the catalytic filter and the cooling system, or both, to remove a portion of water from the gas flow comprising the oxygen.

3. The device of claim 1, wherein the cooling system additionally comprises a heat sink.

4. The device of claim 3, wherein the cooling system comprises one or more fans.

5. The device of claim 1, wherein the condenser is configured for the draining of liquid water throughout the length of the condenser.

6. The device of claim 5, wherein the liquid water is drained from the condenser immediately and continuously.

7. The device of claim 1, wherein the cooling system additionally comprises a receptacle for collecting the condensed water.

8. The device of claim 1, wherein the feed flow regulator comprises a pump.

9. The device of claim 8, wherein the pump is selected from the group consisting of a displacement pump, a peristaltic pump, a syringe pump, a piston pump, a plunger pump, a screw pump and a reciprocating pump.

10. The device of claim 1, wherein the catalyst for the reaction chamber and the catalyst for the catalytic filter are the same catalyst.

11. The device of claim 10, wherein the catalyst is selected from a metal, a metalloid, an alloy of a metal, an alloy of a metalloid, a metal oxide, and a compound of a metalloid, or mixtures thereof.

12. The device of claim 10, wherein the catalyst comprises manganese dioxide.

13. The device of claim 1, wherein the aqueous hydrogen peroxide solution is at least about 15% hydrogen peroxide.

14. The device of claim 13, wherein the aqueous hydrogen peroxide solution is between about 30% to about 70% hydrogen peroxide.

15. The device of claim 2, wherein each of the one or more hydrophobic membranes comprises a material selected from acrylic co-polymers, polytetrafluoroethylene (PTFE), and polyvinylidenedifluoride (PVDF).

16. The device of claim 1, wherein the oxygen flow exiting the device comprises less than about 1 ppm of hydrogen peroxide.

17. The device of claim 16, wherein the oxygen flow exiting the device comprises less than about 0.5 ppm of hydrogen peroxide.

18. The device of claim 1, wherein the oxygen that exits the device is not more than about 10° C. above the ambient temperature.

19. The device of claim 1, wherein the device generates a constant flow of oxygen up to at least about 8 L/min, at a temperature of less than about 40° C. for more than about 30 minutes.

\* \* \* \* \*